US012558331B2

(12) United States Patent　　　(10) Patent No.:　US 12,558,331 B2
Huhtinen et al.　　　　　　　　　(45) Date of Patent:　Feb. 24, 2026

(54) PREGABALIN FORMULATIONS AND USE THEREOF

(71) Applicant: ORION CORPORATION, Espoo (FI)

(72) Inventors: Mirja Huhtinen, Espoo (FI); Terttu Lamminen, Espoo (FI); Jukka Salmia, Espoo (FI); Johanna Tervapuro, Espoo (FI); Jurgen Vercruysse, Zulte (BE)

(73) Assignee: ORION CORPORATION, Espoo (FI)

( * ) Notice: Subject to any disclaimer, the term of this patent is extended or adjusted under 35 U.S.C. 154(b) by 1186 days.

(21) Appl. No.: 17/442,345

(22) PCT Filed: Mar. 26, 2020

(86) PCT No.: PCT/FI2020/050193
§ 371 (c)(1),
(2) Date: Sep. 23, 2021

(87) PCT Pub. No.: WO2020/193864
PCT Pub. Date: Oct. 1, 2020

(65) Prior Publication Data
US 2022/0175707 A1　　Jun. 9, 2022

(30) Foreign Application Priority Data

Mar. 26, 2019　(FI) ..................................... 20195226

(51) Int. Cl.
| | |
|---|---|
| *A61P 25/22* | (2006.01) |
| *A61K 9/00* | (2006.01) |
| *A61K 9/08* | (2006.01) |
| *A61K 31/197* | (2006.01) |
| *A61K 47/12* | (2006.01) |
| *A61K 47/22* | (2006.01) |
| *A61K 47/26* | (2006.01) |
| *A61K 47/46* | (2006.01) |

(52) U.S. Cl.
CPC .......... *A61K 31/197* (2013.01); *A61K 9/0056* (2013.01); *A61K 9/08* (2013.01); *A61P 25/22* (2018.01)

(58) Field of Classification Search
CPC ..... A61P 25/22; A61K 31/197; A61K 9/0056; A61K 9/08; A61K 9/0053; A61K 47/12; A61K 47/22; A61K 47/26; A61K 47/46
See application file for complete search history.

(56) References Cited

FOREIGN PATENT DOCUMENTS

WO　　WO 02/094220 A1　　11/2002

OTHER PUBLICATIONS

Esteban, M. A. et al., "Pharmacokinetics of Single-Dose Oral Pregabalin Administration in Normal Cats," *Frontiers in Veterinary Science*, Jul. 20, 2018, vol. 5, p. 1-6.
International Search Report of International Application No. PCT/FI2020/050193, mail date Jul. 10, 2020 (3 pages).
Taylor, C. P. et al., "Pharmacology and mechanism of action of pregabalin: The calcium channel a2-8 (alpha2-delta) subunit as a target for antiepileptic drug discovery," *Epilepsy Research* (2007) 73, 137-150.

*Primary Examiner* — Sun Jae Yoo
(74) *Attorney, Agent, or Firm* — Finnegan, Henderson Farabow, Garrett & Dunner, LLP

(57) ABSTRACT

The invention relates to a pharmaceutical composition in the form of an orally deliverable liquid composition comprising pregabalin as an active ingredient and to the use thereof in the treatment and prevention of transportation and veterinary visit anxiety and fear in companion animals, such as cats. The composition is stable, well palatable to animals and can be easily administered by the pet owner.

18 Claims, 1 Drawing Sheet

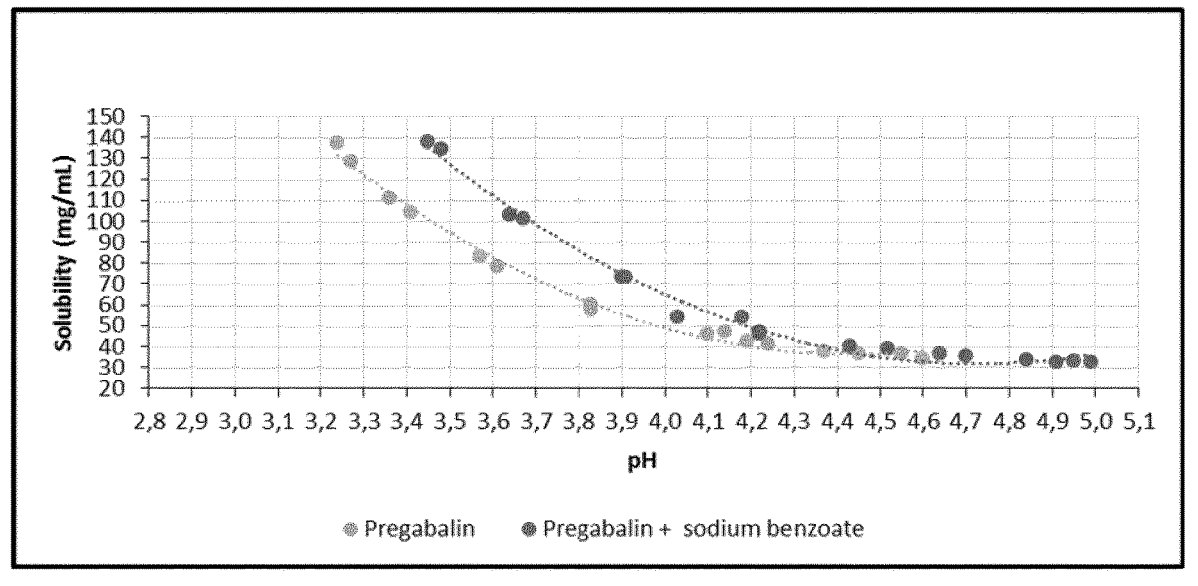

PREGABALIN FORMULATIONS AND USE THEREOF

This is a National Stage Application under 35 U.S.C. § 371 of International Patent Application No. PCT/FI2020/050193, filed Mar. 26, 2020, which claims the benefit of priority of Finnish Patent Application No. 20195226, filed Mar. 26, 2019, both of which are incorporated herein by reference.

TECHNICAL FIELD

The present invention relates to a pharmaceutical composition in the form of an orally deliverable liquid pharmaceutical composition comprising pregabalin as an active ingredient and to the use thereof in the treatment and prevention of transportation and veterinary visit anxiety and fear in companion animals, such as cats.

BACKGROUND OF THE INVENTION

Pet owners find taking their cat to the veterinarian highly stressful for the animal and themselves, with 57% of owners reporting that the cat resists going to the veterinarian. Additionally, cats find veterinary visits stressful. Based on results of a survey study among cat owners most cats show impaired welfare during all stages of a clinic visit: before entering, in the waiting room, moving to the examination room, on the examination table, and after returning home. Distress worsens with every further experience and has negative effects on traveling and handling also in other situations. Restraint, pain, and anxiety lead to aggression toward vets and owners. As many cats aggressively resist being put into carriers and transported to the veterinary clinic, and show signs of stress during veterinary visits, cat owners defer taking their animal to the veterinarian. Based on veterinary care usage study, 40% of cats had not been to the veterinarian within the past year, compared with 15% of dogs. As a group, cats have unmet medical needs, in large part because of the reluctance of owners to subject the cat to the distress of the veterinary visit, and are likely to be more seriously ill than they would otherwise. Fear is causing cats to be underserved by the veterinary profession. Anxiolytic or sedative medications have been used in an attempt to make transportation and veterinary visits less stressful for feline patients, including benzodiazepines (e.g. alprazolam, midazolam, lorazepam), gabapentin, serotonin antagonist and reuptake inhibitors (e.g. trazodone) and clonidine. Medical therapies commonly suggested either involve a long period of onset (several weeks) or cause sedation and/or ataxia as an adverse effect. Currently there are no registered veterinary medicaments in the United States or Europe for treating transportation and veterinary visit anxiety in cats.

Pregabalin, an inhibitor of certain voltage-gated calcium channels, is registered in humans for the treatment of epilepsy, neuropathic pain and generalized anxiety disorder. Use of pregabalin in the treatment of pain in cats has been reported (Lamont, L., Vet Clin Small Anim 38 (2008) 1187-1203). Pregabalin is available for human use as tablets, capsules and as oral solution. The commercially available oral solution of pregabalin for humans has a concentration of 20 mg/ml which would require impractically high amount of solution to be administrated orally to cats.

WO 2002/094220 describes stable liquid compositions of pregabalin having a pH from 5.5 to 7.0 and containing at least one polyhydric alcohol. The authors of this patent application found that degradation of pregabalin (lactam formation) can be substantially avoided at this pH range. Polyhydric alcohol is used as a preservative since common preservatives were found unsuitable due to their low water solubility at this pH range at the required refrigeration storage temperatures (2° C.-8° C.).

WO 2005/063229 describes stable liquid compositions of pregabalin comprising a preservative and a taste-masking agent. The pH of the composition is again in the range from 5.5 to 7.0 to minimize lactam formation. A number of common preservatives and taste-masking agents were found unsuitable for use due to their insufficient water solubility at refrigeration storage temperatures at this pH range. Methylparaben or ethylparaben as a preservative and sodium saccharin as a taste-masking agent was found suitable. Pregabalin concentration of 15 mg/ml is described in the formulation examples.

There is a need for an effective medicament for treating feline transportation and veterinary visit anxiety with rapid onset of action and easy administration such that it can be given by the pet owner, and which does not produce marked ataxia or excessive sedation.

SUMMARY OF THE INVENTION

It has been found that pregabalin, particularly in the form of oral liquid pharmaceutical composition, is effective medicament for treating transportation and veterinary visit anxiety and fear in companion animals such as cats. The oral liquid pharmaceutical composition suitable for treating transportation and veterinary visit anxiety and fear, e.g. in cats, comprises pregabalin at a concentration of at least 35 mg/ml, preferably at least 40 mg/ml, more preferably at least 45 mg/ml. While the literature recommends pH range of 5.5-7.0 for ensuring stability of pregabalin, it was found that the water solubility of pregabalin at this pH range is insufficient for higher concentration liquid compositions needed for oral delivery in cats. However, it was found that the present composition is surprisingly stable at the pH range from about 3.0 to about 4.5 and capable of dissolving considerably higher amounts of pregabalin. Thus, the composition of the present invention is particularly suitable for oral delivery in cats. The composition has rapid onset of action in alleviating feline transportation and veterinary visit anxiety and fear. It does not produce marked ataxia or excessive sedation. The composition is well palatable to cats and can be easily administered by the pet owner.

According to one embodiment of the invention, the present invention provides a liquid pharmaceutical composition adapted for oral administration comprising a) pregabalin as an active ingredient at a concentration of at least 35 mg/ml, preferably at least 40 mg/ml, more preferably at least 45 mg/ml;

b) a flavouring agent;

c) a preservative; and d) water;

wherein the pH of the composition is from about 3.0 to about 4.4, preferably from about 3.1 to about 4.3, more preferably from about 3.2 to about 4.2, still more preferably from about 3.5 to about 4.0.

According to another embodiment of the invention, the present invention provides a method for the treatment or prevention of transportation and veterinary visit anxiety and fear in companion animals, particularly cats, comprising administering to the subject in need thereof an effective amount of a composition comprising pregabalin as an active ingredient.

According to another embodiment of the invention, the present invention provides the use of a composition comprising pregabalin as an active ingredient in the manufacture of a medicament for the treatment or prevention of transportation and veterinary visit anxiety and fear in companion animals, particularly cats.

According to another embodiment of the invention, the present invention provides a composition comprising pregabalin as an active ingredient for use in the treatment or prevention of transportation and veterinary visit anxiety and fear in companion animals, particularly cats.

According to one embodiment of the invention, the present invention provides a medicinal kit comprising a) a liquid pharmaceutical composition adapted for oral administration comprising pregabalin as an active ingredient, b) a package for containing said composition, and c) instructions for administering said composition to a companion animal, particularly cat, for the treatment or prevention of transportation and veterinary visit anxiety and fear.

BRIEF DESCRIPTION OF THE DRAWINGS

FIG. 1 shows water solubility of pregabalin as such and with the addition of 2.0 mg/ml of sodium benzoate as the function of pH at 5° C.

DETAILED DESCRIPTION OF THE INVENTION

The term "transportation anxiety and fear", as used herein, refers to a behavioral syndrome of companion animals, particularly cats, characterized by signs of distress, fear, phobia or aggression when the animal is moved to a transportation vehicle or is traveling in a transportation vehicle, for example car, bus, train or airplane. Such signs include, for example, vocalisation, restlessness, destructive behaviour, hiding, freezing, crouching, panting and sweating paws.

The term "veterinary visit anxiety and fear", as used herein, refers to a behavioral syndrome of companion animals, particularly cats, characterized by signs of distress, fear, phobia or aggression when the animal visits a veterinarian or is examined or treated by a veterinarian. Such signs include, for example, vocalisation, restlessness, struggling, escaping, freezing, crouching and panting.

The term "companion animal", as used herein, refers to an animal suitable for being kept as a pet by humans and includes dog and cat.

The term "pregabalin", as used herein, refers to pregabalin in free form (zwitterion) and to pharmaceutically acceptable salts, complexes, solvates, hydrates and enantiomers thereof.

The term "preservative", as used herein, means a compound that inhibits microbial and/or fungal growth in the solution to which it is added.

The term "buffering agent" or "buffer", as used herein, means a compound or combination of compounds that when dissolved in water, resists changes to pH upon addition of acid or base, compared to water without the buffering agent added upon addition of the same amounts of the same acids and bases.

The term "liquid pharmaceutical composition", as used herein, means a pharmaceutical composition comprising a liquid carrier such as water, wherein the active ingredient, such as pregabalin, is at least partly, preferably completely, solubilized. Thus, in the preferred embodiment, "liquid pharmaceutical composition" is an aqueous solution.

The present invention provides a liquid pharmaceutical composition adapted for oral administration comprising
 a) pregabalin as an active ingredient at a concentration of at least 35 mg/ml, preferably at least 40 mg/ml, more preferably at least 45 mg/ml;
 b) a flavouring agent;
 c) a preservative; and
 d) water;
 wherein the pH of the composition is from about 3.0 to about 4.4, preferably from about 3.1 to about 4.3, more preferably from about 3.2 to about 4.2, still more preferably from about 3.5 to about 4.0.

According to one embodiment of the invention, the above composition is a veterinary liquid pharmaceutical composition adapted for oral administration to a companion animal, particularly cat. The composition is, in particular, adapted to be voluntarily consumed by a cat as such or as mixed with food. The composition is particularly useful for the treatment or prevention of transportation and veterinary visit anxiety and fear in companion animals, particularly cats.

The amount of composition to be administered is suitably selected such as to provide sufficient transportation and veterinary visit anxiety and fear alleviating effect while not causing marked ataxia or excessive sedation in the treated animal. Accordingly, for the treatment or prevention of transportation and veterinary visit anxiety and fear in companion animals, such as cats, pregabalin is administered generally in an amount of about 0.5-20 mg/kg, preferably about 1-10 mg/kg, more preferably about 2-8 mg/kg, and typically about 4-6 mg/kg, for example about 5 mg/kg. The composition is suitably administered from about 0.5 to about 2 hours before the occurrence of transportation or veterinary visit.

According to one embodiment of the invention, the composition according to the invention comprises pregabalin as a sole active ingredient.

According to one other embodiment of the invention, the composition according to the invention may comprise in addition to pregabalin one or more other active ingredient (s), particularly those useful in the treatment or prevention of transportation and veterinary visit anxiety and fear in companion animals, particularly cats.

The composition according to the invention is preferably in the form of an aqueous solution adapted for oral administration companion animals, particularly cats. The concentration of pregabalin should be high enough such that no impractically high amount of solution needs to be administrated orally to companion animals, particularly cats. Thus, the concentration of pregabalin in the aqueous solution composition is at least 35 mg/ml, preferably at least 40 mg/ml, more preferably at least 45 mg/ml. For example, the concentration of pregabalin is generally within the range from about 35 mg/ml to about 150 mg/ml, preferably from about 40 mg/ml to about 100 mg/ml, more preferably from about 45 mg/ml to about 80 mg/ml, for example about 50 mg/ml.

It was found that water solubility of pregabalin is improved in the composition of the invention having lower pH value. The pH of the composition is suitably in the range from about 3.0 to about 4.4, preferably from about 3.1 to about 4.3, more preferably from about 3.2 to about 4.2, still more preferably from about 3.5 to about 4.0, for example about 3.7. At this pH range pregabalin was found to be stable in the composition of the present invention at refrigerator conditions. The pH of the composition can be adjusted to the desired range, for example, by using a pH adjusting agent. A pH adjusting agent may be a simple base or acid which does not have a pH buffering ability by itself, e.g. NaOH or HCl. Alternatively, the pH adjusting agent can be a buffering agent having ability to buffer the pH of the solution to the desired pH value. Suitable buffering agents include, for example, lactic acid/lactate, citric acid/citrate or acetic acid/acetate buffers. Buffers are suitably used in an amount of about 0.1-5%, preferably about 0.2-3%, for example about 0.5-2%, per weight of the composition. The buffers should be selected such that they do not have any negative effect on the palatability of the formulation to the companion animals such as cats. It was, however, found that the pregabalin solution according to the present invention maintains its pH value well even without any additional buffering agent due to the buffering ability of pregabalin itself.

The composition suitably also comprise a preservative to inhibit microbial and/or fungal growth in the solution. The preservative is selected from agents that are physicochemically stable and active in the required pH range, do not have any negative effect on the palatability of the formulation and are compatible with the other components of the formulation. Examples of preservatives include benzoic acid and salts thereof such as sodium benzoate or potassium benzoate, sorbic acid and salts thereof such as potassium sorbate. Preservatives are commonly used in an amount of 0.01-1%, preferably 0.05-0.5%, for example 0.1-0.2%, per weight of the composition. It was found that benzoic acid salts such as sodium benzoate are particularly preferred preservatives. In addition to having a preservative activity, benzoic acid salts such as sodium benzoate were found to improve the physical stability of pregabalin by inhibiting precipitation of pregabalin in the composition of the invention. Benzoic acid salts such as sodium benzoate are preferably used in an amount of about 0.05-0.2% per weight of the composition.

As pregabalin has strong bitter taste, the composition preferably comprises one or more flavouring agents. The flavouring agent is suitably selected such that it improves the palatability of the solution to companion animals, particularly cats. In order to maintain the composition in the form of solution, the flavouring agent should also be water soluble, stable and compatible with the other components of the composition. Flavouring agents are generally used in an amount of about 0.001-10%, preferably about 0.002-5%, more preferably about 0.002-1%, per weight of the composition.

It is known that cats are not attracted by sugars and sweeteners and they probably are unable to taste the sweetness of sugars due to lack of the relevant receptor gene (Li, X. et al., (2005), PLoS Genet., 1(1), e3, 0027-0035). In contrast, yeast extract and hydrolysed yeast have shown to have good palatability for both dogs and cats. However, most yeast products available are not particularly suitable components of pharmaceutical dosage forms. They are typically multicomponent products manufactured from natural sources and make the pharmaceutical analysis of the dosage form difficult. They also suffer from significant batch-to-batch variation and may cause discoloration of pharmaceutical solutions.

Ethyl maltol was found to be particularly suitable as a flavoring agent for the pharmaceutical solution of the invention. It is compatible with the other components of the solution, is water-soluble, stable and is unexpectedly palatable to companion animals, particularly cats, even though it is characterized by a sweet flavor. Moreover, it needs be used in very small amounts in order to make the composition palatable. Ethyl maltol is suitably used in an amount of from about 0.001 to about 0.05%, preferably from about 0.002 to about 0.01%, for example from about 0.002% to about 0.006, per weight of the composition.

The composition may further comprise antioxidants such as butylated hydroxyanisole (BHA) or butylated hydroxytoluene (BHT), chelating agents such as edetate disodium, thickening agents such as sodium carboxymethylcellulose and other ingredients commonly used in the preparation of solutions for oral administration.

According to one embodiment, the invention provides a veterinary liquid pharmaceutical composition adapted for oral administration to companion animals, particularly cats, comprising
   (i) about 3.5-15%, preferably about 4-10%, more preferably from about 4.5-8%, per weight of the composition, of pregabalin;
   (ii) about 0.001-10%, preferably about 0.002-5%, more preferably about 0.002-1%, per weight of the composition, of a flavouring agent;
   (iii) about 0.01-1%, preferably about 0.05-0.5%, more preferably about 0.1-0.2%, per weight of the composition, of a preservative; and
   (iv) about 75-96.5%, preferably about 85-96%, more preferably about 90-95.5%, per weight of the composition, of water,
   wherein the pH of the composition is from about 3.0 to about 4.4, preferably from about 3.1 to about 4.3, more preferably from about 3.2 to about 4.2, still more preferably from about 3.5 to about 4.0.

According to another embodiment, the invention provides a veterinary liquid pharmaceutical composition adapted for oral administration to companion animals, particularly cats, comprising
   (i) about 3.5-15%, preferably about 4-10%, more preferably from about 4.5-8%, per weight of the composition, of pregabalin;
   (ii) about 0.001-0.05%, preferably about 0.002-0.01%, more preferably about 0.002-0.006, per weight of the composition, of ethyl maltol;
   (iii) about 0.05-0.5%, preferably about 0.1-0.2%, per weight of the composition, of a benzoic acid salt; and
   (iv) about 85-96.5%, preferably about 90-96%, more preferably about 92-95.5%, per weight of the composition, of water,
   wherein the pH of the composition is from about 3.0 to about 4.4, preferably from about 3.1 to about 4.3, more preferably from about 3.2 to about 4.2, still more preferably from about 3.5 to about 4.0.

According to still another embodiment, the invention provides a veterinary liquid pharmaceutical composition adapted for oral administration to companion animals, particularly cats, comprising
   (i) pregabalin as an active ingredient at a concentration of at least 35 mg/ml, preferably at least 40 mg/ml, more preferably at least 45 mg/ml;
   (ii) ethyl maltol;
   (iii) sodium benzoate; and
   (iv) water;
   wherein the pH of the composition is from about 3.0 to about 4.4, preferably from about 3.1 to about 4.3, more preferably from about 3.2 to about 4.2, still more preferably from about 3.5 to about 4.0.

According to one preferred embodiment of the invention, the liquid pharmaceutical composition according to any of the embodiments above is an aqueous solution, i.e. a composition where pregabalin is in completely solubilized form.

The liquid pharmaceutical compositions according to the invention can be prepared e.g. by dissolving the active ingredient and excipients to water under stirring, followed by pH adjustment, if necessary, and filtering.

The composition can be provided in the form of medicinal kit comprising a) a liquid pharmaceutical composition adapted for oral administration comprising pregabalin as an active ingredient, b) a package for containing said composition, and c) instructions for administering said composition to a companion animal, particularly cat, for the treatment or prevention of transportation and veterinary visit anxiety and fear.

The invention is further illustrated by the following examples, which are not meant to limit the scope of the invention.

Formulation Example 1

| | Quantity mg/ml |
| --- | --- |
| Pregabalin | 50 |
| Sodium benzoate | 2.0 |
| Ethyl maltol | 0.04 |
| Hydrochloric acid 10% and/or Sodium hydroxide 2M | q.s. ad pH 3.7 |
| Purified water | ad 1 ml |

Formulation Example 2

| | Quantity mg/ml |
| --- | --- |
| Pregabalin | 50 |
| Sodium benzoate | 2.0 |
| Ethyl maltol | 0.04 |
| Lactic acid | 1.8 |
| Hydrochloric acid 10% and/or Sodium hydroxide 2M | q.s. ad pH 3.7 |
| Purified water | ad 1 ml |

Formulation Example 3

| | Quantity mg/ml |
| --- | --- |
| Pregabalin | 50 |
| Sodium benzoate | 2.0 |
| Yeast extract | 5 |
| Hydrochloric acid 10% and/or Sodium hydroxide 2M | q.s. ad pH 3.7 |
| Purified water | ad 1 ml |

Formulation Example 4

| | Quantity mg/ml |
| --- | --- |
| Pregabalin | 50 |
| Sodium benzoate | 2.0 |
| Yeast extract | 5 |
| Lactic acid | 1.8 |
| Hydrochloric acid 10% and/or Sodium hydroxide 2M | q.s. ad pH 3.7 |
| Purified water | ad 1 ml |

8

The above formulations were prepared by dissolving the excipients and drug substance in purified water followed by adjusting the pH, when necessary.

Experiment 1. Solubility of Pregabalin

Water solubility at 5° C. of pregabalin as such and with the addition of 2.0 mg/ml sodium benzoate was measured as the function of pH. The results are shown in FIG. 1. The water solubility of pregabalin increased significantly when pH is lower than about 4.4. It can be also seen that sodium benzoate further improved the physical stability of pregabalin by inhibiting precipitation of pregabalin.

Experiment 2. Stability Study

The chemical and physical stability of Formulation Example 1 was compared to commercial pregabalin 20 mg/ml human oral solution (Lyrica®) at 2–8° C. in glass bottle. It can be seen that stability of Formulation Example 1 containing pregabalin 50 mg/ml and having pH about 3.7 was comparable to the stability of the commercial pregabalin product (Lyrica®) containing pregabalin 20 mg/ml and having pH about 6.1.

TABLE 1

Stability of Formulation Example 1 compared to commercial pregabalin 20 mg/ml human oral solution (Lyrica ®) at 2-8° C.

| Product | Time point | Appearance | pH | Assay % | Related substances, Impurity A (lactam) % |
| --- | --- | --- | --- | --- | --- |
| Formulation Example 1 | 0 month | Clear transparent solution | 3.71 | 99.6 | <LOQ* |
| | 6 months | Clear transparent solution | 3.69 | 102.0 | <LOQ |
| | 12 months | Clear transparent solution | 3.70 | 100.0 | 0.07 |
| Lyrica ® | 0 month | Clear transparent solution | 6.13 | 99.7 | <LOQ |
| | 6 months | Clear transparent solution | 6.02 | 99.2 | <LOQ |
| | 12 months | Clear transparent solution | 6.11 | 99.9 | <LOQ |

*LOQ (limit of quantification) <0.05%

Experiment 3. Palatability Study

Palatability study of Formulation Examples 2, 3 and 4 in cats (n=12) was performed. Formulation was offered to cats in 5 mg/kg dose. If the cat had not consumed the whole dose voluntarily without food within 5 min (more than 50% of dose remaining) the product was given with food. If the cat had not consumed the product with food voluntarily within 5 min (more than 50% of the pellets remaining), the product was given with syringe. The results of the study are shown in Table 1. For each animal, the portion of the dose consumed is shown. It can be seen that the formulation of the Formulation Example 2 (with ethyl maltol) appeared most palatable.

TABLE 2

| Palatability of Formulation Examples 4, 3 and 2 in cats. | | | | | | |
|---|---|---|---|---|---|---|
| | Example 4 | | Example 3 | | Example 2 | |
| Animal ID. | Alone | With feed | Alone | With feed | Alone | With feed |
| 006767 | 1 | / | 1 | / | 1 | / |
| 008923 | 0 | 1 | 0 | 1 | 0 | 1 |
| 005911 | 0 | 1 | 0.33 | 1 | 0.33 | 1 |
| 115276 | 0 | 1 | 0 | 1 | 0 | 1 |
| 012376 | 0 | 1 | 0 | 1 | 0.33 | 1 |
| 012371 | 0.33 | 1 | 0 | 1 | 0.33 | 1 |
| 004209 | 0.33 | 1 | 0 | 0,3 | 0 | 1 |
| 061525 | 0 | 1 | 0 | 1 | 0 | 1 |
| 078503 | 0 | 1 | 0 | 1 | 0 | 1 |
| 349198 | 0 | 1 | 0.33 | 1 | 0.33 | 1 |
| 352866 | 0.33 | 0.5 | 0 | 0.8 | 0 | 1 |
| 436224 | 0 | 1 | 0 | 1 | 0 | 1 |
| Total alone | 1.99 | | 1.66 | | 2.32 | |
| Total with feed | | 9.5 | | 10.1 | | 11 |
| Total voluntary intake | 11.49 | | 11.76 | | 13.32 | |

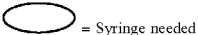 = Syringe needed

Experiment 4. Clinical Study in Cats

A randomized, double-blind, placebo-controlled parallel-group, multicenter clinical study was conducted for evaluating the efficacy and safety of pregabalin for the treatment or prevention of transportation and veterinary visit anxiety and fear in cats. Cats were randomised to receive either 5 mg/kg (n=108) of pregabalin or placebo (n=101) orally as a single dose approximately 90 minutes before transportation to the veterinary clinic.

The study had two primary efficacy variables. The first primary variable was the owner's assessment of the treatment effect based on the cat's stress, anxiety and/or fear during transportation in a car. The second primary variable was the investigator's assessment of the treatment effect based on the cat's stress, anxiety and/or fear during clinical examination at the veterinary clinic. Both were assessed using a numerical rating scale with the scores 1-5.

The results of the primary variables are presented in Table 3. A statistically significant treatment effect favouring pregabalin 5 mg/kg against placebo was seen in both primary variables: the owner's assessment of treatment effect during transportation (p=0.0010) and the investigator's assessment of treatment effect during clinical examination (p=0.0003). Pregabalin 5 mg/kg did not produce marked ataxia or excessive sedation.

TABLE 3

| Clinical study results in cats. | | | | |
|---|---|---|---|---|
| | Owner's assessment of treatment effect during transportation % of cats | | Investigator's assessment of treatment effect during clinical examination % of cats | |
| Score | 5 mg/kg | Placebo | 5 mg/kg | Placebo |
| 1 Excellent | 17.1 | 5.9 | 14.3 | 1.0 |
| 2 Good | 34.3 | 20.8 | 41.0 | 28.7 |
| 3 Fair | 23.8 | 27.7 | 27.6 | 44.6 |

TABLE 3-continued

| Clinical study results in cats. | | | | |
|---|---|---|---|---|
| | Owner's assessment of treatment effect during transportation % of cats | | Investigator's assessment of treatment effect during clinical examination % of cats | |
| Score | 5 mg/kg | Placebo | 5 mg/kg | Placebo |
| 4 Poor | 14.3 | 29.7 | 10.5 | 11.9 |
| 5 Very poor | 10.5 | 15.8 | 6.7 | 13.9 |

The invention claimed is:

1. A liquid pharmaceutical composition adapted for oral administration comprising:
   (i) pregabalin as an active ingredient at a concentration of at least 35 mg/ml;
   (ii) a flavouring agent;
   (iii) a preservative; and
   (iv) water;
   wherein the pH of the composition is from about 3.0 to about 4.4.

2. The composition according to claim 1, wherein the composition is a veterinary liquid pharmaceutical composition adapted for oral administration to a companion animal.

3. The composition according to claim 1, wherein the composition comprises 3.5-15%, per weight of the composition, of pregabalin.

4. The composition according to claim 1, wherein the flavouring agent is yeast extract, hydrolysed yeast, or ethyl maltol.

5. The composition according to claim 4, wherein the flavouring agent is ethyl maltol.

6. The composition according to claim 1, wherein the preservative is a benzoic acid salt.

7. The composition according to claim 6, wherein the preservative is sodium benzoate.

8. The composition according to claim 1, wherein the composition lacks a buffering agent other than pregabalin itself.

9. The composition according to claim 1, wherein the composition comprises:
   (i) pregabalin as an active ingredient at a concentration of at least 35 mg/ml;
   (ii) ethyl maltol;
   (iii) sodium benzoate; and
   (iv) water;
   wherein the pH of the composition is from about 3.0 to about 4.4.

10. The composition according to claim 1, wherein the composition comprises:
   (i) 3.5-15%, per weight of the composition, of pregabalin;
   (ii) 0.002-1%, per weight of the composition, of the flavouring agent;
   (iii) 0.01-1%, per weight of the composition, of the preservative; and
   (iv) 75-96.5%, per weight of the composition, of sterile water;
   wherein the pH of the composition is from about 3.0 to about 4.4.

11. The composition according to claim 9, wherein the composition comprises:
   (i) 3.5-15%, per weight of the composition, of pregabalin;
   (ii) 0.001-0.05%, per weight of the composition, of ethyl maltol;

(iii) 0.05-0.5%, per weight of the composition, of a benzoic acid salt; and (iv) 85-96.5%, per weight of the composition, of sterile water, wherein the pH of the composition is from about 3.0 to about 4.4.

12. A method for the treatment or prevention of transportation and veterinary visit anxiety and fear in a companion animal comprising administering to the companion animal in need thereof an effective amount of the liquid pharmaceutical composition according to claim 1.

13. A medicinal kit comprising a) the liquid pharmaceutical composition according to claim 1, b) a package for containing said composition, and c) instructions for administering said composition to a companion animal for the treatment or prevention of transportation and veterinary visit anxiety and fear.

14. The composition according to claim 1, wherein the composition comprises pregabalin as an active ingredient at a concentration of at least 40 mg/ml.

15. The composition according to claim 1, wherein the composition comprises pregabalin as an active ingredient at a concentration of at least 45 mg/ml.

16. The composition according to claim 1, wherein the pH of the composition is from about 3.2 to about 4.2.

17. The composition according to claim 1, wherein the pH of the composition is from about 3.5 to about 4.0.

18. The composition according to claim 2, wherein the companion animal is a cat.

* * * * *